United States Patent [19]

Zaiger et al.

[11] Patent Number: Plant 6,764

[45] Date of Patent: Apr. 25, 1989

[54] PLUM TREE

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 138,649

[22] Filed: Dec. 28, 1987

[51] Int. Cl.[4] ..... A01H 5/03

[52] U.S. Cl. ..... Plt./38

[58] Field of Search ..... Plt./38

*Primary Examiner*—Robert E. Bagwill

[57] ABSTRACT

Our new development relates to a distinct variety of plum tree which has the following unique combination of desirable features:

1. The large size of fruit throughout the tree.
2. Heavy and regular production of fruit.
3. Fruit that will stay firm on the tree 2–3 weeks after picking ripe.
4. Fruit with a high degree of attractive blackish blue skin color.
5. The fruit having firm flesh and good shipping quality.
6. Fruit with good flavor and eating quality.

1 Drawing Sheet

ORIGIN OF THE VARIETY

The present new and distinct variety of plum tree was originated by us in the experimental orchard located at Modesto, Calif., from a cross between Laroda Plum (non-patent) and Queen Ann Plum (non-patent). The selection was made from a large group of seedlings that were grown and maintained under careful observation, during which time we recognized the desirable characteristics described above and selected the present variety for reproduction and commercialization.

ASEXUAL REPRODUCTION OF THE VARIETY

The present variety of plum tree was asexually reproduced by budding at the experimental orchard located at Modesto, Calif. and shows that all characteristics run true to form and are established and transmitted through succeeding propagations.

SUMMARY OF THE VARIETY

Our present variety of plum tree is of large size, vigorous, upright growth and a productive and regular bearer of large, clingstone fruit, characterized as to novelty by being nearly uniform in size throughout the tree, having attractive blackish blue skin color, with firm flesh and good eating, shipping and storage quality and maturing approximately 10 days before Queen Ann Plum (non-patent).

DESCRIPTION OF THE PHOTOGRAPHS

The accompanying photographs show reproductions in color of the fruit and foliage of our new plum variety, with the upper and lower surface of the leaves being illustrated and the exterior and a cross sectional view of a fruit divided in the suture plane to reveal flesh coloration and showing a stone remaining in place. The photographs were taken shortly after being picked at maturity (firm ripe) and the colors are as nearly true as is reasonably possible in a color illustration of this type.

DESCRIPTION OF THE VARIETY

The following is a botanical description of our new variety of plum tree, its foliage and fruit as based on observations of the specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Bearer.*—Regular.
- *Production.*—Productive.

Trunk:
- *Size.*—Medium to large.
- *Surface.*—Medium shaggy.
- *Color.*—Grayish brown.

Branches:
- *Size.*—Medium.
- *Surface.*—Medium rough.
- *Lenticels.*—Medium number. Medium size.
- *Color.*—Grayish brown to brown.

Leaves:
- *Size.*—Medium to large. Average length — 4" to 4¾". Average width — 1 3/8" to 1½".
- *Form.*—Mostly elliptical. Some oblanceolate.
- *Texture.*—Smooth.
- *Margin.*—Finely serrate.
- *Petiole.*—Size — medium. Average length — 1". Average width — 1/16".
- *Glands.*—Globose. Number varies from 1 to 3. Average number 2. Located on lower part of leaf blade and upper part of petiole.
- *Color.*—Upper surface — dark green (27-F-6) to (27-F-8). Lower surface — grayish green (27-E-6) to (27-E-7).

Flower buds:
- *Size.*—Medium.
- *Length.*—Medium.
- *Shape.*—Medium to short Plump.

Flowers:
- *Blooming period.*—Mar. 5, 1987 to Mar. 10, 1987. Varies slightly with climatic conditions.
- *Pollen.*—Present.
- *Color.*—White.
- *Size.*—Medium.

Fruit:

*Maturity when described.*—Firm ripe.

*Date of first picking.*—Jun. 23, 1987.

*Date of last picking.*—Jul. 1, 1987.

*Size.*—Large. Average diameter axially — $2\frac{1}{2}''$ to $2\frac{3}{4}''$. Average transversely in suture plane — $2\frac{1}{2}''$ to $2\frac{3}{4}''$.

*Form.*—Globose.

*Suture.*—Shallow. Extends from base to apex.

*Cavity.*—Rounded to slightly elongated in suture plane. Average depth — $1\frac{1}{2}''$. Average breadth — $\frac{5}{8}''$.

*Base.*—Rounded to slight retuse.

*Apex.*—Usually rounded. Varies from retuse to slight point.

*Stem.*—Average length — $\frac{3}{4}''$. Average width — 3/32".

Skin:

*Thickness.*—Medium.

*Texture.*—Tough — tenacious to flesh.

*Tendency to crack.*—None.

*Down.*—Wanting.

*Color.*—Dark reddish blue to blackish blue (18-F-6) to (18-F-8).

Flesh:

*Ripen.*—Evenly.

*Texture.*—Firm — meaty.

*Juice.*—Moderate.

*Eating quality.*—Good.

*Flavor.*—Good.

*Color.*—Pale yellow to light yellow (4-A-3) to (4-A-5). Pit cavity — yellowish brown (5-E-5) to (5-E-6).

Stone:

*Type.*—Clingstone.

*Size.*—Medium. Average length — 1". Average width — $\frac{3}{4}''$. Average thickness — $\frac{5}{8}''$.

*Form.*—Ovid.

*Apex.*—Acuminate.

*Base.*—Usually straight

*Sides.*—Mostly equal.

*Surface.*—Small irregular furrows with slight ridges near ventral surface.

*Tendency to split.*—None.

*Color.*—Light brown (6-D-5) to (6-D-7).

Use:

*Market.*—Local and long distance. Dessert.

Storage quality: Good.

Shipping quality: Good.

The new variety of plum tree and its fruit herein described may vary in slight detail due to climatic, soil conditions and cultural practices under which the variety may be grown. The present description is that of the variety grown and fruit produced under ecological conditions prevailing at Modesto, Calif.

We claim:

1. A new and distinct variety of plum tree, substantially as illustrated and described, characterized by its large size, vigorous, upright growth and being a productive and regular bearer of large size, firm, clingstone fruit with good eating, storage and shipping quality; the fruit is further characterized by being nearly uniform in size throughout the tree, nearly globose in shape with an attractive blackish blue skin color and maturing approximately 10 days before Queen Ann Plum (non-patent).

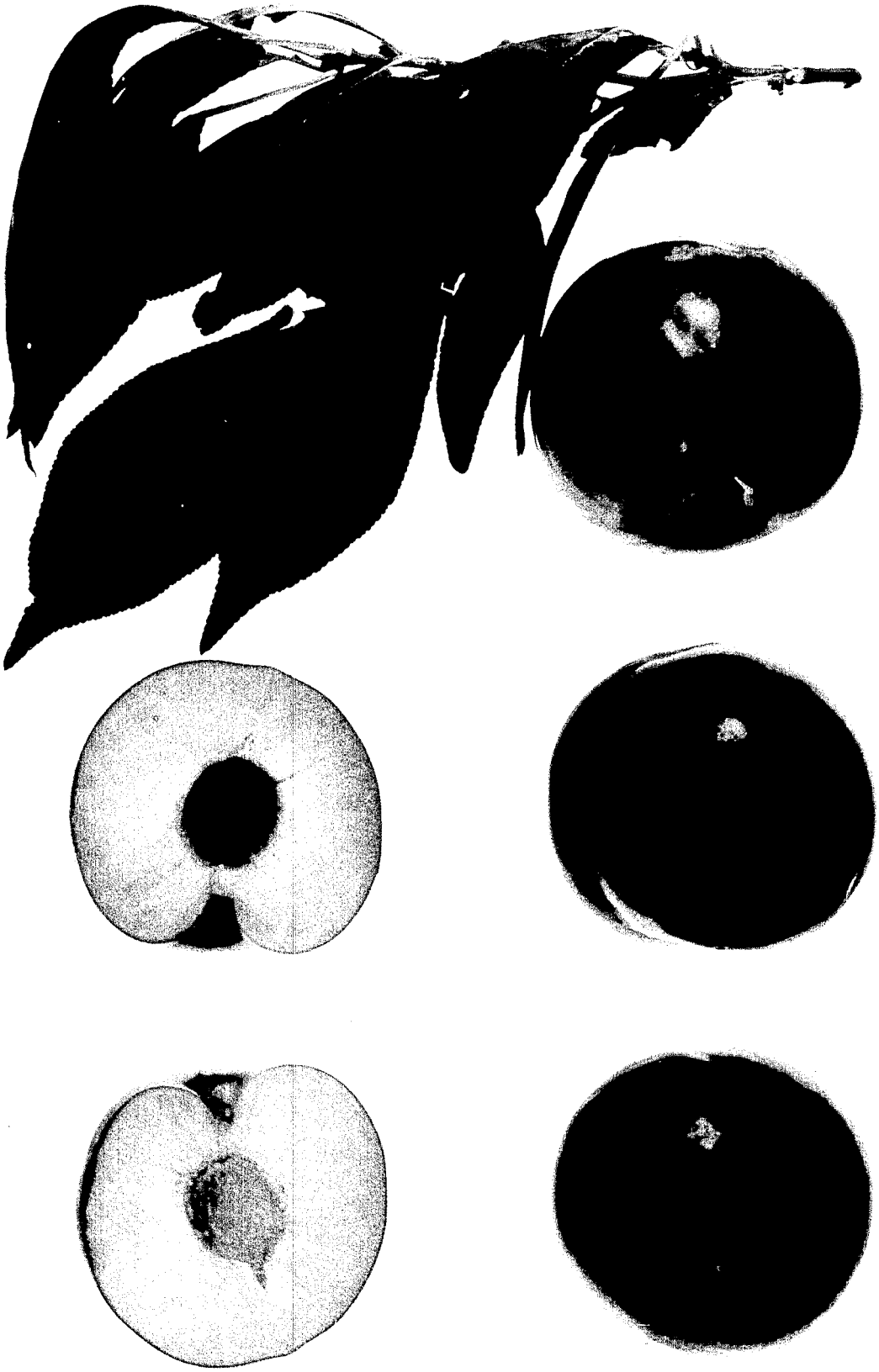

* * * * *